(12) United States Patent
Arendt et al.

(10) Patent No.: US 9,370,766 B2
(45) Date of Patent: Jun. 21, 2016

(54) SORBENT COMPRISING ON ITS SURFACE AN ALIPHATIC UNIT FOR THE PURIFICATION OF ORGANIC MOLECULES

(71) Applicant: INSTRACTION GMBH, Mannheim (DE)

(72) Inventors: Markus Arendt, Hockenheim (DE); Björn Degel, Hassloch (DE); Thomas Schwarz, Leichlingen (DE); Gerhard Stumm, Hamburg (DE); Martin Welter, Heidelberg (DE)

(73) Assignee: INSTRACTION GMBH, Janderstrasse, Mannheim (DE)

( * ) Notice: Subject to any disclaimer, the term of this patent is extended or adjusted under 35 U.S.C. 154(b) by 0 days.

(21) Appl. No.: 14/344,425

(22) PCT Filed: Sep. 17, 2012

(86) PCT No.: PCT/EP2012/068197
§ 371 (c)(1),
(2) Date: Mar. 12, 2014

(87) PCT Pub. No.: WO2013/037993
PCT Pub. Date: Mar. 21, 2013

(65) Prior Publication Data
US 2015/0045533 A1    Feb. 12, 2015

(30) Foreign Application Priority Data

Sep. 15, 2011 (EP) ..................... 11181413

(51) Int. Cl.
| | | |
|---|---|---|
| *B01D 15/32* | (2006.01) | |
| *B01J 20/26* | (2006.01) | |
| *B01J 20/32* | (2006.01) | |
| *C07D 498/12* | (2006.01) | |
| *C07K 14/625* | (2006.01) | |
| *A61K 31/436* | (2006.01) | |
| *B01J 20/287* | (2006.01) | |
| *B01J 20/286* | (2006.01) | |
| *B01D 15/38* | (2006.01) | |

(52) U.S. Cl.
CPC ............. *B01J 20/328* (2013.01); *A61K 31/436* (2013.01); *B01D 15/32* (2013.01); *B01D 15/327* (2013.01); *B01J 20/267* (2013.01); *B01J 20/286* (2013.01); *B01J 20/287* (2013.01); *B01J 20/3219* (2013.01); *B01J 20/3246* (2013.01); *B01J 20/3248* (2013.01); *B01J 20/3272* (2013.01); *B01J 20/3282* (2013.01); *B01J 20/3285* (2013.01); *C07D 498/12* (2013.01); *C07K 14/625* (2013.01); *B01D 15/3804* (2013.01)

(58) Field of Classification Search
None
See application file for complete search history.

(56) References Cited

U.S. PATENT DOCUMENTS

| | | | |
|---|---|---|---|
| 4,920,152 A * | 4/1990 | Regnier et al. | 521/31 |
| 5,100,547 A | 3/1992 | Hardiman | |
| 5,245,008 A | 9/1993 | Dickhardt | |
| 6,074,555 A | 6/2000 | Boos | |
| 2002/0164712 A1 * | 11/2002 | Gan | 435/69.4 |
| 2007/0151928 A1 * | 7/2007 | Glad et al. | 210/656 |
| 2008/0262614 A1 * | 10/2008 | Marchant et al. | 623/11.11 |
| 2009/0042318 A1 | 2/2009 | Tanaka | |
| 2009/0155370 A1 * | 6/2009 | Cope et al. | 424/497 |
| 2009/0218276 A1 * | 9/2009 | Linford et al. | 210/506 |
| 2010/0136072 A1 * | 6/2010 | Haldar et al. | 424/402 |
| 2011/0151493 A1 * | 6/2011 | Cockrill | 435/23 |

FOREIGN PATENT DOCUMENTS

| | | |
|---|---|---|
| EP | 2003455 | 12/2008 |
| WO | WO 98/48914 | 11/1998 |
| WO | WO 2011/012302 | 2/2011 |

OTHER PUBLICATIONS

International Search Report for PCT/EP2012/068197 of Oct. 30, 2012.

* cited by examiner

*Primary Examiner* — Jeffrey E Russel
(74) *Attorney, Agent, or Firm* — Hueschen and Sage

(57) ABSTRACT

The present invention relates to a sorbent comprising a solid support material, the surface of which comprises a residue of a general formula (I), wherein the residue is attached via a covalent single bond to a functional group on the surface of either the bulk solid support material itself or of a polymer film on the surface of the solid support material. Furthermore, the present invention relates to the use of the sorbent according to the invention for the purification of organic molecules, in particular pharmaceutically active compounds, preferably in chromatographic applications.

6 Claims, 7 Drawing Sheets

Figure 1:
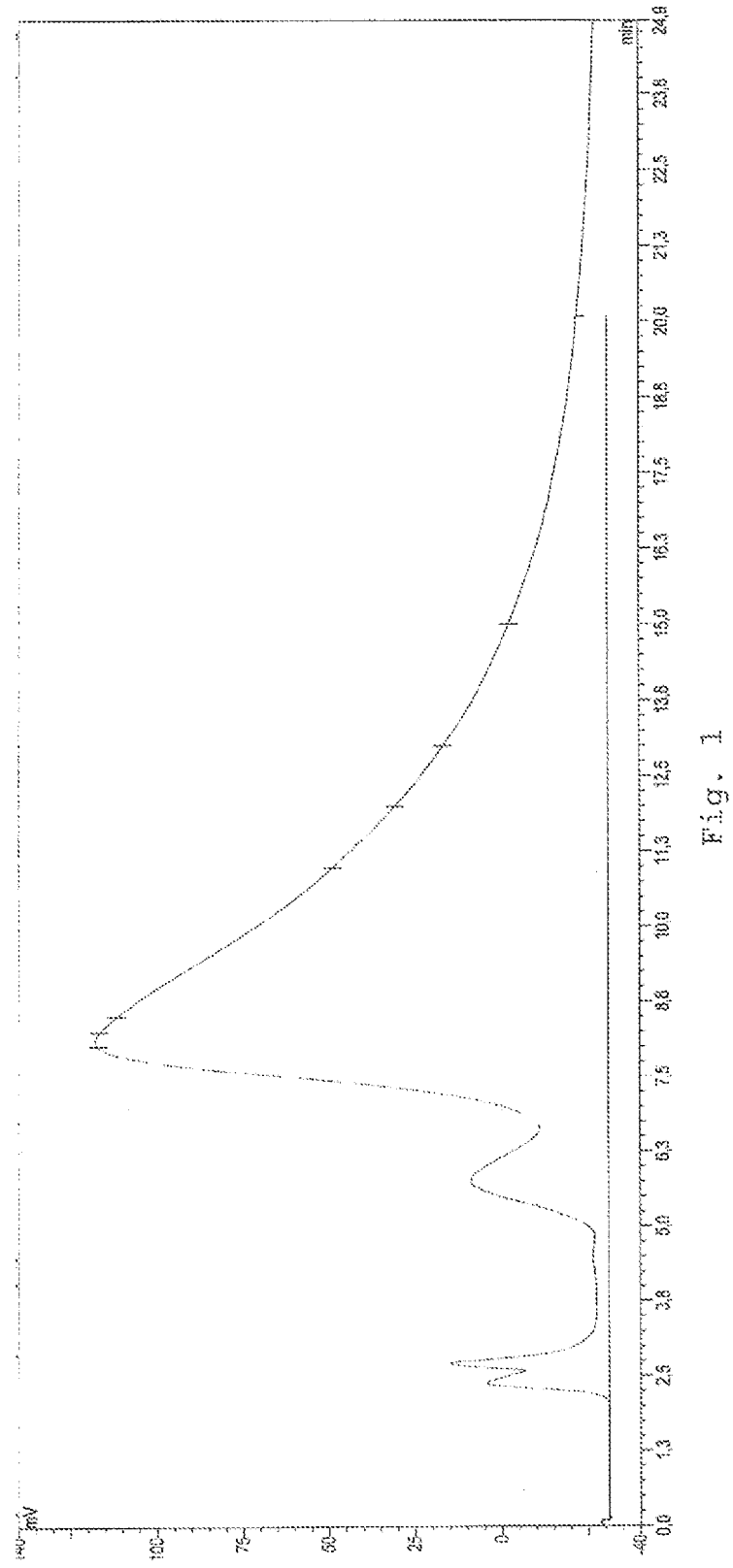

SORBENT COMPRISING ON ITS SURFACE AN ALIPHATIC UNIT FOR THE PURIFICATION OF ORGANIC MOLECULES

The present invention relates to a sorbent comprising a solid support material, the surface of which comprises a residue of a general formula (I), wherein the residue is attached via a covalent single bond to a functional group on the surface of either the bulk solid support material itself or of a polymer film on the surface of the solid support material. Furthermore, the present invention relates to the use of the sorbent according to the invention for the purification of organic molecules, in particular pharmaceutically active compounds, preferably in chromatographic applications.

Chromatography media for organic molecules and biomolecules have traditionally been categorized according to one or more of the following possible modes of interaction with a sample:
hydrophobic interaction (reversed phase)
hydrophilic interaction (normal phase)
cation exchange
anion exchange
size exclusion
metal ion chelation.

The provision of new chemical compounds, either by its discovery in plant extracts or animals or, by chemical synthesis, always demands the provision of new chromatographic materials, the further development of known chromatographic materials or the finding of a new way for the purification of the chemical compounds which is simple and cost-effective. That is, there is always a demand for new highly selective downstream purification technologies capable of handling large capacities without up-scaling the required volumes of liquid by the same factor.

Traditional stepwise application of the above chromatographic categories to a given separation problem was accordingly mirrored in a step-by-step, steady improvement of the product purity but also in product losses at every stage which accumulate seriously in the end, not to mention the operational time and cost of goods. Introduction of affinity chromatography at an early stage into the downstream process could be an answer to this demand since the reduction of a consecutive series of sequential chromatography steps into only one could thus be demonstrated many times. Affinity chromatography is sometimes regarded as a class of its own although, from a chemical point of view, it is based on the same interaction modes as above, but usually on a combination of two or more modes. By using affinity chromatography the specific interactions between an analyte and the sorbent may be verified both between the analyte and active residues bound on the surface of a matrix of the chromatographic material and between the analyte and surface characteristics of the matrix itself.

Affinity chromatography has mostly been carried out with bulk gel-phase resins. Pre-eminent gel-forming materials are medium-crosslinked polysaccharides, polyacrylamides, and poly(ethylene oxides). Such hydrogels often ensure a compatible interface which can well accommodate both the active residue of the ligand and the analyte interacting therewith due to their softness (conformational flexibility, elastic modulus), large pore systems, high polarity and high water content, as well as the absence of reactive or denaturing chemical groups. They are able to retain analytes, such as proteins, in their native state, i.e. preserve their correctly folded, three-dimensional structure, state of association, and functional integrity, or do not chemically change the structure of a complex pharmaceutically active compound. The mechanical resistance of these media is, however, much weaker than that of inorganic support materials since they are compressible under an applied pressure and do not tolerate shear stress caused by agitation, column packing or high liquid flow rates. Affinity sorbents that are fully compatible with robust HPLC process conditions are therefore rare.

Only in the recent past it has been recognised that the mechanical resistance of the stationary phase is a bulk property of the sorbent support whereas only a thin layer at the interface between the stationary and the mobile phases is responsible for mass exchange and for the interaction with the biological analyte. Therefore the concept of combining the function of a mechanically very rigid and dimensionally stable, porous 3-dimensional core, and a biocompatible, gel-like interlace layer which carries the active residues for binding the analyte has been brought up, and the associated synthetic problems have been technically solved. Such hybrid materials employ loosely crosslinked polymers of high polarity on a base of either an inorganic oxide or a densely crosslinked polymer of low polarity.

It was an object of the present invention to provide a new sorbent for chromatographic applications which allows the simple and cost-effective purification of organic molecules, even when used in chromatographic applications which demand a high stability of the material either with regard to the mechanic stress or in view of the solution characteristics of the eluent.

The present invention therefore provides a sorbent comprising a solid support material, the surface of which comprises a residue of the following general formula (I):

$$\text{------L-X} \qquad \text{formula (I)},$$

wherein the residue is attached via a covalent single bond represented by the dotted line in formula (I) to a functional group on the surface of either the bulk solid support material itself or of a polymer film on the surface of the solid support material, depending on whether the solid support material comprises a polymeric film or not; and
wherein the used symbols and parameters have the following meanings:
L represents a covalent single bond or is a bivalent unit selected from the group consisting of —C(O)—, —S(O)$_2$—, —CH$_2$CH(OH)— and —C(O)NH—;
X represents a monovalent linear aliphatic hydrocarbon group having 1 to 30 carbon atoms or branched or cyclic aliphatic hydrocarbon group having 3 to 30 carbon atoms; wherein
one or more, preferably one, CH$_2$-moieties in said group may be substituted by O, S, —S(O)$_2$—, —C(O)NH— or —C(S)NH—;
one or more hydrogen atoms may be substituted by F, Cl, Br, —CN or —NC; and
said group may comprise one or more double bonds between two carbon atoms.

In one embodiment according to the invention it is preferred that the residue according to formula (I) is attached via a covalent single bond to the functional group of a polymer film on the surface of the solid support material.

An monovalent linear aliphatic hydrocarbon group having 1 to 30 carbon atoms or branched or cyclic aliphatic hydrocarbon group having 3 to 30 carbon atoms preferably is one of the following groups: methyl, ethyl, n-propyl, iso-propyl, n-butyl, iso-butyl, sec-butyl (1-methylpropyl), tert-butyl, iso-pentyl, n-pentyl, tert-pentyl (1,1-dimethylpropyl), 1,2-dimethylpropyl, 2,2-dimethylpropyl (neopentyl), 1-ethylpropyl, 2-methylbutyl, n-hexyl, iso-hexyl, 1,2-dimethylbutyl, 1-ethyl-1-methylpropyl, 1-ethyl-2-methylpropyl, 1,1,2-trimethylpropyl, 1,2,2-trimethylpropyl, 1-ethylbutyl, 1-methylbutyl, 1,1-dimethylbutyl, 2,2-dimethylbutyl, 1,3-dimethylbutyl, 2,3-dimethylbutyl, 3,3-dimethylbutyl, 2-ethylbutyl, 1-methylpentyl, 2-methylpentyl, 3-methylpentyl, 1-methylpentyl, n-heptyl, n-octyl, n-nonyl, n-decyl, n-undecyl, n-dodecyl, n-tridecyl, n-tetradecyl, n-pentadecyl, 1-hexylnonyl, n-hexadecyl, 1-hexyl-decyl, n-heptadecyl, n-octadecyl, n-nonadecyl, —$(CH_2)_{20}CH_3$, —$(CH_2)_{21}CH_3$, —$(CH_2)_{22}CH_3$, cyclopentyl, cyclohexyl, cycloheptyl, cyclooctyl, 2-ethylhexyl, trifluormethyl, pentafluorethyl, 2,2,2-trifluorethyl, ethenyl, propenyl, butenyl, pentenyl, cyclopentenyl, hexenyl, cyclohexenyl, heptenyl, cycloheptenyl, octenyl or cyclooctenyl, wherein one or more, preferably one, $CH_2$-moieties in said groups may be substituted by a group having a hydrogen donor and/or a hydrogen acceptor moiety, such as O, S, —$S(O)_2$—, —C(O)NH— or —C(S)NH—, and wherein one or more hydrogen atoms may be substituted by F, Cl, Br, —CN or —NC, wherein F and —CN is preferred.

It is preferred that X is an monovalent linear aliphatic hydrocarbon group having 1 to 22 carbon atoms, or a monovalent linear branched or cyclic aliphatic hydrocarbon group having 3 to 20 carbon atoms, wherein
- one or more, preferably one, $CH_2$-moieties in said group may be substituted by O, S, —$S(O)_2$—, —C(O)NH— or —C(S)NH—;
- one or more hydrogen atoms may be substituted by F, Cl, Br, —CN or —NC; and/or
- said group may comprise one or more double bonds between two carbon atoms.

It is further preferred that X is a linear or branched aliphatic hydrocarbon group having 1 to 22 carbon atoms or 3 to 22 carbon atoms, respectively, wherein it is further preferred that X is a linear aliphatic hydrocarbon group having 1 to 22 carbon atoms. As mentioned above one or more, preferably one, $CH_2$-moieties in said group may be substituted by O, S, —$S(O)_2$—, —C(O)NH— or —C(S)NH— and one or more hydrogen atoms may be substituted by F, Cl, Br, —CN or —NC, wherein F and —CN is more preferred.

It is, however, more preferred that the aliphatic hydrocarbon group is a linear or branched alkyl. According to this invention an alkyl is free of heteroatoms.

A linear alkyl is preferably a $C_1$-$C_{22}$-alkyl which means a group with the formula —$(CH_2)_n CH_3$, wherein n is 1 to 22, wherein it is preferred that n is 6 to 15, even more preferred 8 to 13, and most preferred 11.

A branched alkyl is preferably a $C_3$-$C_{22}$-alkyl which means a group wherein at least one tertiary or quaternary carbon atom is present which binds either to further carbon atoms or L.

Preferred examples of the branched $C_3$-$C_{22}$-alkyl are: iso-propyl, iso-butyl, sec-butyl (1-methylpropyl), tert-butyl, iso-pentyl, tert-pentyl (1,1-dimethylpropyl), 1,2-dimethylpropyl, 2,2-dimethylpropyl (neopentyl), 1-ethylpropyl, 2-methylbutyl, iso-hexyl, 1,2-dimethylbutyl, 1-ethyl-1-methylpropyl, 1-ethyl-2-methylpropyl, 1,1,2-trimethylpropyl, 1,2,2-trimethylpropyl, 1-ethylbutyl, 1-methylbutyl, 1,1-dimethylbutyl, 2,2-dimethylbutyl, 1,3-dimethylbutyl, 2,3-dimethylbutyl, 3,3-dimethylbutyl, 2-ethylbutyl, 1-methylpentyl, 2-methylpentyl, 3-methylpentyl, 4-methylpentyl, 1-hexylnonyl and 1-hexyl-decyl.

In case that one or more $CH_2$-moieties in the aliphatic hydrocarbon group is substituted by O, S or —$S(O)_2$—, it is preferred that at most 30 mol-% of the $CH_2$-moieties are substituted by one or more, preferably one, of these groups, based on all $CH_2$-moieties and the substituted groups together. Preferred examples for these groups are: —($C_1$-$C_8$-alkylene)-Y—($C_1$-$C_{15}$-alkyl) or —($C_1$-$C_6$-alkylene)-O— ($CH_2CH_2O)_b$—($C_1$-$C_{15}$-alkyl), wherein Y is O, S or —$S(O)_2$, $C_1$-$C_8$-alkylene means a unit —$(CH_2)_m$—, wherein m is 1 to 6, $C_{1-15}$-alkyl means a group —$(CH_2)_k$—$CH_3$, wherein k is 1 to 15, and h is 1 to 20.

As mentioned above L represents a covalent single bond or is a bivalent unit having a hydrogen donor and/or a hydrogen acceptor moiety. The bivalent unit is preferably selected from the group consisting of —C(O)—, —$S(O)_2$—, —$CH_2CH(OH)$— and —C(O)NH—, more preferred —C(O)—, —$S(O)_2$— and —$CH_2CH(OH)$—, even more preferred —C(O)— and —$S(O)_2$—, and most preferred —C(O)—. In case L represents a covalent single bond the group X directly binds to the functional group of the solid support material. In case L represents one of the units —C(O)—, —$S(O)_2$—, —$CH_2CH(OH)$— and —C(O)NH—, it is preferred that the first mentioned atom having a free ending line is connected in this position to the solid support material and the second mentioned atom having a free ending line is connected in this position to X.

It is particularly preferred that at least one of L and X comprises one of the above-mentioned groups comprising a hydrogen donor and/or hydrogen acceptor moiety. This is important from the view that the surface of the sorbent according to the invention comprises the possibility to bind compounds via hydrogen bonds on the one hand and via hydrophobic interactions by means of the aliphatic moiety of X on the other hand. This ensures that compounds can be purified that have both hydrophobic and hydrophilic moieties in its structure. Therefore, in case L represents a covalent single bond, it is preferred that at least one of the $CH_2$-moieties of the aliphatic group X is substituted by a group having a hydrogen donor and/or a hydrogen acceptor moiety. In case L represents one of the units having a hydrogen donor and/or a hydrogen acceptor moiety, X is preferably a linear or branched alkyl.

In one embodiment of the sorbent according to the invention it is preferred that L is —C(O)— and X is a linear or branched, preferred a linear, aliphatic hydrocarbon group having 1 to 22 carbon atoms or 3 to 22 carbon atoms, respectively, more preferred a linear $C_1$-$C_{22}$-alkyl or branched $C_3$-$C_{22}$-alkyl, further preferred a linear $C_1$-$C_{22}$-alkyl, wherein $C_6$-$C_{15}$-alkyl is even more preferred, a $C_8$-$C_{13}$-alkyl is still more preferred and $C_{11}$-alkyl is most preferred.

In an embodiment the sorbent according to the present invention only comprises residues according to formula (I).

In an embodiment the sorbent of the present invention may comprise a further residue which may be another residue according to formula (I), but may also be a residue different from the residues according to formula (I), such as for example a residue comprising an aromatic or heteroaromatic group.

The solid support material is preferably a macroporous material. The pore size of the solid support material is preferably at least 6 nm, more preferably from 10 to 400 nm and most preferably from 10 to 250 nm. A pore size in this range is important to ensure that the purification capacity is high enough. If the pore size is over the above higher limit the more of the polymer on the surface must be cross-linked leading to a polymer which is not flexible enough. It is believed that then the binding groups may not be able to come into a position which is important to sufficiently bind the compounds to be purified. In case the pore site is too low, the polymer film may clog the pores and the effect of the porosity of the sorbent is lost.

According to an embodiment of the sorbent according to the invention, the solid support material has a specific surface area of from 1 m²/g to 1000 m²/g, more preferred of from 30 m²/g to 800 m²/g and most preferred of from 50 to 500 m²/g.

It is preferred that the solid support material has a porosity of from 30 to 80% by volume, more preferred from 40 to 70% by volume and most preferred from 50 to 60% by volume. The porosity can be determined by mercury intrusion according to DIN 66133. The pore size of the solid support material can also be determined by pore filling with the mercury intrusion method according to DIN 66133. The specific surface area can be determined by nitrogen adsorption with the BET-method according to DIN 66132.

The solid support material many be an organic polymeric material or an inorganic material. Especially in case that the sorbent according to the invention comprises more than one residue, the solid support material is preferably an inorganic material.

In case the solid support material is a polymeric material, it is substantially non-swellable. For that reason, it is mostly preferred that the polymeric material has a high crosslinking degree.

The polymeric material is preferably crosslinked at a degree of at least 5%, more preferably at least 10% and most preferably at least 15%, based on the total number of crosslinkable groups in the polymeric material. Preferably, the crosslinking degree of the polymeric material does not exceed 50%.

Preferably the polymeric material for the solid support material is selected from the group consisting of generic or surface-modified polystyrene, (e.g. poly(styrene-co-divinylbenzene)), polystyrene sulfonic acid, polyacrylates, polymethacrylates, polyacrylamides, polyvinylalcohol, polysaccharides (such as starch, cellulose, cellulose esters, amylose, agarose, sepharose, mannan, xanthan and dextran), and mixtures thereof.

The polymeric material possibly used in the present invention preferably has before the crosslinking has been performed 10 to 10000, particularly preferably 20 to 5000 and very particularly preferably 50 to 2000 repeat units. The molecular weight $M_w$ of the polymeric material before the crosslinking has been performed is preferably in the range of 10000 to 2000000 g/mol, particularly preferably in the range of 100000 to 1500000 g/mol, and very particularly preferably in the range of 200000 to 1000000 g/mol. The determination of $M_w$ can be performed according to standard techniques known to the person skilled in the art by employing gel permeation chromatography (GPC) with polystyrene as internal standard, for instance.

In case the solid support material is an inorganic material, the inorganic material is some kind of inorganic mineral oxide, preferably selected from the group consisting of silica, alumina, magnesia, titania, zirconia, fluorosile, magnetite, zeolites, silicates (cellite, kieselguhr), mica, hydroxyapatite, fluoroapatite, metal-organic frameworks, ceramics and glasses, like controlled pore glass (e.g. trisoperl), metals such as aluminium, silicon, iron, titanium, copper, silver, gold and also graphite or amorphous carbon.

Independent of whether the solid support material is a polymeric material or an inorganic material, the solid support material provides a solid base of a minimum rigidity and hardness which functions as an insoluble support and provides a basis for the enlargement of the interface between stationary and mobile phases which is the place of interaction with the analyte as the molecular basis for the process of the partitioning between said phases, and for an increased mechanical strength and abrasiveness, especially under flow and/or pressurised conditions.

The solid support materials according to the invention may be of homogeneous or heterogeneous composition, and therefore also incorporate materials which are compositions of one or more of the materials mentioned above, in particular multi-layered composites.

The solid support material may be a particulate material, preferably having a particle size of from 5 to 500 µm. The solid support material may also be a sheet- or fibre-like material such as a membrane. The external surface of the solid support material thus may be flat (plates, sheets, foils, disks, slides, filters, membranes, woven or nonwoven fabrics, paper) or curved (either concave or convex: spheres, beads, grains, (hollow) fibres, tubes, capillaries, vials, wells in a sample tray).

The pore structure of the internal surface of the solid support material may, inter alia, consist of regular, continuous capillary channels or of cavities of irregular (fractal) geometry. Microscopically, it can be smooth or rough, depending on the way of manufacture. The pore system can either extend continuously throughout the entire solid support material or end in (branched) cavities. The rate of an analyte's interfacial equilibration between its solvation in the mobile phrase and its retention on the surface of the stationary phase and thus the efficiency of a continuous flow separation system is largely determined by mass transfer via diffusion through the pores of the solid support material and thus by its characteristic distribution of particle and pore sizes. Pore sizes may optionally show up as asymmetric, multimodal and/or spatially (e.g. cross-sectionally) inhomogeneous distributions.

As mentioned above, the surface of the solid support material is preferably covered with a film of a polymer. The polymer comprises or consists of individual chains which are preferably covalently crosslinked with each other. Furthermore, the polymer is preferably not covalently bound to the surface of the solid support material. The inventors of the present invention have surprisingly found that especially for the purification of compounds having both a hydrophobic and a hydrophilic moiety it is important that the polymer is flexible enough to come into a conformation which makes it possible that both the hydrophobic and the hydrophilic (e.g. hydrogen donor or acceptor interactions) moieties may come into contact with the hydrophobic and hydrophilic moieties of the compound to be purified. In case a polymer film would be used which is covalently bound to the surface of the support material the inventors of the present invention observed that the purification capacity significantly decreased. That is, the use of a non-covalently surface bound cross-linked polymer as a polymer film has three advantages: (1) Flexibility of the polymer due to the fact that it is not surface bound; (2) the cross-linking ensures that the film is adhered to the surface of the support material and is not lost; (3) the thickness of the polymer can be adjusted as thin as wanted, if the polymer is not covalently bound to the polymer.

It is further preferred that the polymer covering the support material is a hydrophilic polymer. Hydrophilic properties of the polymer ensure that the hydrophilic interactions between the sorbent and the compound to be purified can take place.

The polymer for the crosslinkable polymer is preferably assembled by at least monomers comprising a hydrophilic group, preferably in its side chain. Preferred hydrophilic groups are —NH₂, —NH—, —OH, —COOH, —OOCCH₃, anhydrides, —NHC(O)— and saccharides, wherein —NH₂ and —OH is more preferred and —NH₂ is most preferred.

If co-polymers are employed, the preferred co-monomers are simple alkene monomers or polar, inert monomers like vinyl pyrrolidone.

Examples of polymers covering the support material are: polyamines, such as polyvinylamine, polyethylene imine, polyallylamine, polyamine acids, such as polylysin etc. as well as functional polymers other than those containing amino groups, such as polyvinyl alcohol, polyvinyl acetate, polyacrylic acid, polymethacrylic acid, their precursor polymers such as poly(maleic anhydride), polyamides, or polysaccharides (cellulose, dextran, pullulan etc.), wherein polyamines such as polyvinylamine and polyallylamine are more preferred and polyvinylamine is most preferred.

With respect to a superior purification capacity it is further preferred that in the sorbent according to the invention the molar ratio of the residues according to formula (I) to the amount of functional groups of the polymer (derivatization degree) is preferably in the range of 0.4 to 0.8, more preferred in the range of 0.5 to 0.7, wherein the amount of residues according to formula (I) is determined by elemental analysis and the amount of functional groups is determined by titration of the sorbent before the residues according to formula (I) have been applied.

Furthermore, the sorbent according to the invention preferably contains residues according to formula (I) in the range of from 40 to 240 µmol/mL, more preferred in the range of from 70 to 210 µmol/mL, related to the total volume of the sorbent, wherein the amount is determined by elemental analysis.

The amount of free functional groups of the sorbent according to the invention is in the range of from 5 to 190 µmol/mL, rebated to the total volume of the sorbent. This amount as determined by titration. The discrepancy between the amount of free functional groups 1) determinable from the molar ratio above and the amount of residues according to formula (I) and 2) the value determined directly by titration is due to the differences in determination via elemental analysis and via titration.

The polymer can be applied to the macroporous support by all means of coating known to a person skilled in the art such as absorption, vapor phase deposition, polymerization from the liquid, gas or plasma phase, spin coating, surface condensation, wetting, soaking, dipping, rushing, spraying, damping, evaporation, application of electric fields or pressure, as well as methods based on molecular self-assembly such as, for example, liquid crystals, Langmuir Blodgett- or layer-by-layer film formation. The polymer may thereby be coated directly as a monolayer or as multilayer or as a stepwise sequence of individual monolayers on top of each other. It is preferred in the present invention that the polymer is coated to the support material in that the non-cross-linked polymer is given to the support material in an aqueous solution and then cross-linked.

The ratio of the weight of the polymer covering the support material to the weight of the support material preferably ranges from 0.005 to 0.15, more preferably 0.01 to 0.08, in the sorbent according to the invention. If the above ratio is above the upper limit, the polymer film is too thick and the pores of the support material are totally covered resulting in a sorbent having no available pores. If the above ratio is below the lower limit, the amount of polymer is not enough to cover the entire support material. Furthermore, in the latter case more crosslinking agent would have to be used in order to fix the polymer to the support material, again resulting in a polymer film not being flexible enough.

According to a preferred embodiment of the sorbent according to the invention, the crosslinking degree of the crosslinked polymer is at least 2%, based on the total number of crosslinkable groups in the crosslinked polymer. More preferred the crosslinking degree is of from 5 to 50%, more preferred of from 5 to 30%, most preferred from 10 to 20%, based on the total number of crosslinkable groups in the crosslinked polymer. The crosslinking degree can easily be adjusted by the stoichiometric amount of the crosslinking reagent used. It is assumed that nearly 100 mol % of the crosslinker reacts and forms crosslinks. This can be verified by analytical methods. The crosslinking degree can be determined by MAS-NMR spectroscopy and quantitative determination of the amount of crosslinker in relation to the amount of polymer. This method is most preferred. The crosslinking degree can also be determined by IR spectroscopy based on e.g. C—O—C or OH vibrations using a calibration curve. Both methods are standard analytical methods for a person skilled in the art. If the crosslinking degree is above the upper limit the polymer film is not flexible enough resulting in an inferior purification capacity. If the crosslinking degree is below the limit mentioned above the film is not sufficiently stable on the surface of the support material.

The crosslinking reagent used for crosslinking the polymer is preferably selected from the group consisting of dicarboxylic acids, diamines, diols, urea and bis-epoxides, more preferred dicarboxylic acids and bis-epoxides, such as terephthalic acic, biphenyl dicarboxylic acid, 1,12-bis-(5-norbornen-2,3-dicarboximido)-decandicarboxylic acid and ethylene glycol diglycidylether, ethylene glycol diglycidylether being most preferred. In one embodiment the at least one crosslinking reagent is a linear, conformationally flexible molecule of a length of between 4 and 20 atoms.

Preferred molecular weights of the polymers used range from, but are not limited to, 5000 to 50000 g/mol, which is particularly true for polyvinylamine. Polymers having a molecular weight near the lower limit of the range given above have shown to penetrate even narrow pores of the carrier so that solid state materials with high surface areas and consequently with good mass transfer kinetics, resolution and binding capacity can be used in the sorbents of the present invention.

According to a further embodiment the crosslinked polymer carries functional groups, i.e. the hydrophilic groups mentioned above.

The term "functional group" means any simple, distinct chemical moiety belonging to the crosslinked polymer on the surface of the solid support material or to the crosslinkable polymer during preparation of a polymer film on the surface of the solid support material. Thereby, the functional group may serve as chemical attachment point or anchor. Functional groups preferably contain at least one weak bond and/or one heteroatom, preferably a group behaving as nucleophil or electrophil.

The preferred functional groups are primary and secondary amino, hydroxyl, and carboxylic acid or ester groups, when taken before the residues of formula (I) have been bound to these groups. When the residues are bound to the functional groups the nature of these groups change with respect to the structure of the residues bound.

The invention also relates to a method for preparing a sorbent, preferably the sorbent according to the invention, comprising:
(i) providing a polymer having functional groups;
(ii) adsorbing a film of said polymer onto the surface of a carrier;
(iii) crosslinking a defined portion of said functional groups of the adsorbed polymer with at least one crosslinking reagent;
(iv) derivatising further defined portions of said functional groups of the crosslinked polymer with one or more residues according to the formula (I).

The polymer to be adsorbed on the surface of the carrier is preferably solved in an aqueous media wherein the pH is suitably adjusted in order to solve or suspend the polymer. The adsorbing of the polymer on the surface of the carrier is preferably done by dipping the carrier into the solution or suspension containing the polymer. The mixture is then preferably shaked in order to get a complete mix of the ingredients. Capillaric forces make sure that pores of the carrier are soaked with the solution or suspension. Then, the water is preferably evaporated in vacuum at a temperature between 40 and 60° C. thereby depositing the polymer at the walls of the pores in the form of a film. Then, the coated material is preferably suspended in an organic solvent, such as isopropanol or dimethylformamide. (DMF), and is preferably crosslinked by means of a crosslinking agent, such as ethylene glycol diglycidyl ether, preferably at a temperature between 25 and 60° C. for 4 to 8 hours.

Depending on the kind of functional groups and depending on the residue according to formula (I) different derivatization strategies of the solid support can be used. If the solid support material contains amino groups as functional groups, residues containing a carboxylic acid group can be attached to the amine nitrogen atom via the carboxylic carbon atom via peptide chemistry using coupling reagents like 2-(1H-benzotriazole-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), benzotriazole-1-yl-oxy-tris-pyrrolidino-phosphonium hexafluorophosphate (PyBOP), propylphosphonic anhydride (T3P) etc. or by using reactive groups in the reagent like isocyanates, epoxides on anhydrides. If the solid support material contains amino groups, aliphatic carbon atoms of the residue according to formula (I) may be bound to the amine nitrogen atom via a nucleophilic aliphatic substitution.

If the solid support material contains hydroxy groups, residues according to formula (I) containing a carboxylic acid group before being attached to the functional group may be attached to the oxygen atom of the hydroxy group via the carboxylic carbon atom by using the carboxylic acid chloride or the ester of the carboxylic acid group. If the solid support material contains hydroxy groups, aliphatic carbon atoms of the residue according to formula (I) may be bound to the oxygen atom of the hydroxy group via a nucleophilic alliphatic substitution.

The person skilled in the field of organic synthesis knows possible reactions of functional groups of the support material with precursor compounds of the residues according to formula (I) in order to obtain the sorbents according to the invention.

The sorbent of the present invention may be used for the purification of organic molecules (organic compounds), or the purification of solutions from certain organic molecules. That is, the present invention further refers to the use of a sorbent according to the invention for the purification of organic molecules, peptides or the purification of solutions from organic molecules.

The term "organic molecules" may not only include organic compounds of low molecular weight, but also biomolecules, such as peptides and enzymes.

The term "purification" is referred to as comprising separating, or increasing the concentration and/or purity of a organic molecule from a mixture containing said organic molecule.

To other words the present invention is also directed to a method of purification of organic molecules which also includes the separation of unwanted organic molecules from a solution by using the sorbent of the present invention.

The use of the sorbent according to the invention for the purification of organic molecules or the method for the purification of organic molecules by using the sorbent according to the invention comprises the following steps:

(i) applying a crude mixture comprising the organic molecules being dissolved or suspended in a liquid on a chromatographic column containing the sorbent according to the invention or a sorbent prepared according to a method of the invention;

(ii) elution of the organic molecule from the column by using an eluent.

The eluent used in step (ii) may be the same solvent as used for the liquid in step (i), but may also be different, depending on the conditions necessary for the purification of the organic molecules. As liquid in step (i) or eluent in step (ii) every kind of solvent or buffering systems applicable in the field of chromatography may be used. In the present invention organic solvents are preferred, especially ethyl acetate and dichloromethane, etc.

The organic molecules purified by means of the sorbent of the present invention are preferably pbarmaceutically active compounds.

The organic molecules to be purified are preferably compounds having a hydrophilic and a hydrophobic moiety in its molecule. More preferably the organic molecules are compounds having beneath a hydrophobic hydrocarbon moiety groups which are able to act as hydrogen donor or hydrogen acceptor. The organic molecule is preferably a compound having one or more of the moieties selected from the groups consisting of —OH, —O—, —S— and —C(O)—.

The organic molecules have preferably a molecular weight in the range of from 500 to 200000 g/mol, more preferably in the range of from 500 to 150000 g/mol, and most preferred of from 500 to 6000 g/mol.

Particularly preferred as organic molecules used in the use/process of the present invention is everolimus or derivatives of everolimus, more preferably everolimus of the following structure:

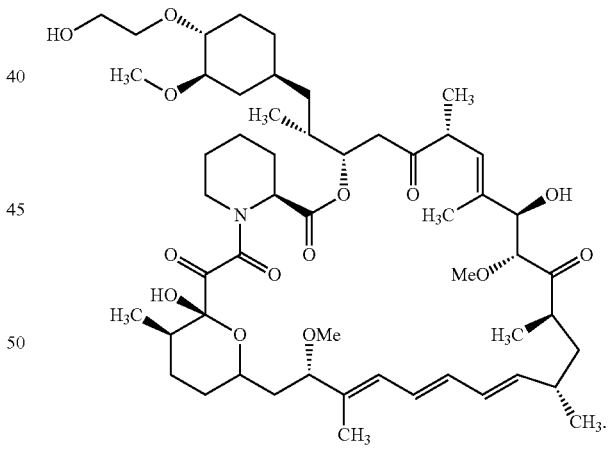

Furthermore, the sorbent according to the invention may also be used for separating endotoxins from solutions. The term "endotoxins" as used in the present invention refers to a class of biochemical substances. Endotoxins are decomposition products of bacteria, which may initiate variable physiologic reactions in humans. Endotoxins are components of the outer cell membrane (OM) of c ram-negative bacteria or blue-green algae. From the chemical view endotoxins are lipopolysaccharides (LPS) which are composed of a hydrophilic polysaccharide component and a lipophilic lipide component. In contrast to the bacteria endotoxins stem from, endotoxins are very thermally stable and endure sterilisation.

The currently most sensitive method of measuring endotoxins is made by means of the activation of the coagulation cascade in the lysate of amoebocytes which have been isolated from limulus polyphemus. This test is commonly known as the so-called LAL-test.

Even preferred in the present invention is the use of the sorbent according to the invention for the purification of insulin from its byproducts.

The invention also relates to a column for liquid chromatography or solid phase extraction comprising a sorbent according to the invention or a sorbent prepared according to a method according to the invention as a stationary phase within a tabular containment and optionally further components such as frits, filter plates, flow distributors, seals, fittings, screwings, valves, or other fluid handling or connection elements. In one embodiment, the method is further characterised by its physical and chemical resistance against applied pressures up to 20 bar, against applied heat up to 110° C., as well as against common sanitisation protocols, thus enabling its repetitive use of up to 1,000 times, preferably up to 5,000 times. The invention also relates to a collection of a plurality of the same or different sorbents according to the invention or of sorbents prepared according to a method according to the invention or of columns according to the invention in the format of a microplate or microchip array, or a multi-capillary or microfluidic device, capable of being processed in parallel.

The invention also relates to a diagnostic or laboratory purification kit comprising a sorbent according to the invention or a sorbent prepared according to a method according to the invention or a column according to the invention or a collection ox sorbents or columns according to the invention and, within the same packaging unit, further chemical or biological reagents and/or disposables necessary for carrying out the method according to the invention or a different analytical, diagnostic, or laboratory method different therefrom.

The present invention further refers to the following embodiments:
(i) A method for the purification of organic molecules using a sorbent according to the invention.
(ii) The method according to embodiment (i), wherein the organic molecules are pharmaceutically active compounds.
(iii) The method according to embodiment (i) or (ii), wherein the organic molecules have a molecular weight in the range of from 500 to 200000 g/mol.
(iv) The method according to any one of the embodiments (i) to (iii), wherein the organic molecules are selected from the group consisting of everolimus, derivatives of everolimus, insulin, derivatives of insulin and endotoxins.

The present invention is further explained by means of the following figures and examples which should however not be understood, as being limiting for the scope of the present invention:

FIGURES

FIG. 1: Chromatogram of the fractionation of everolimus according to Example 2.

Figure 2:
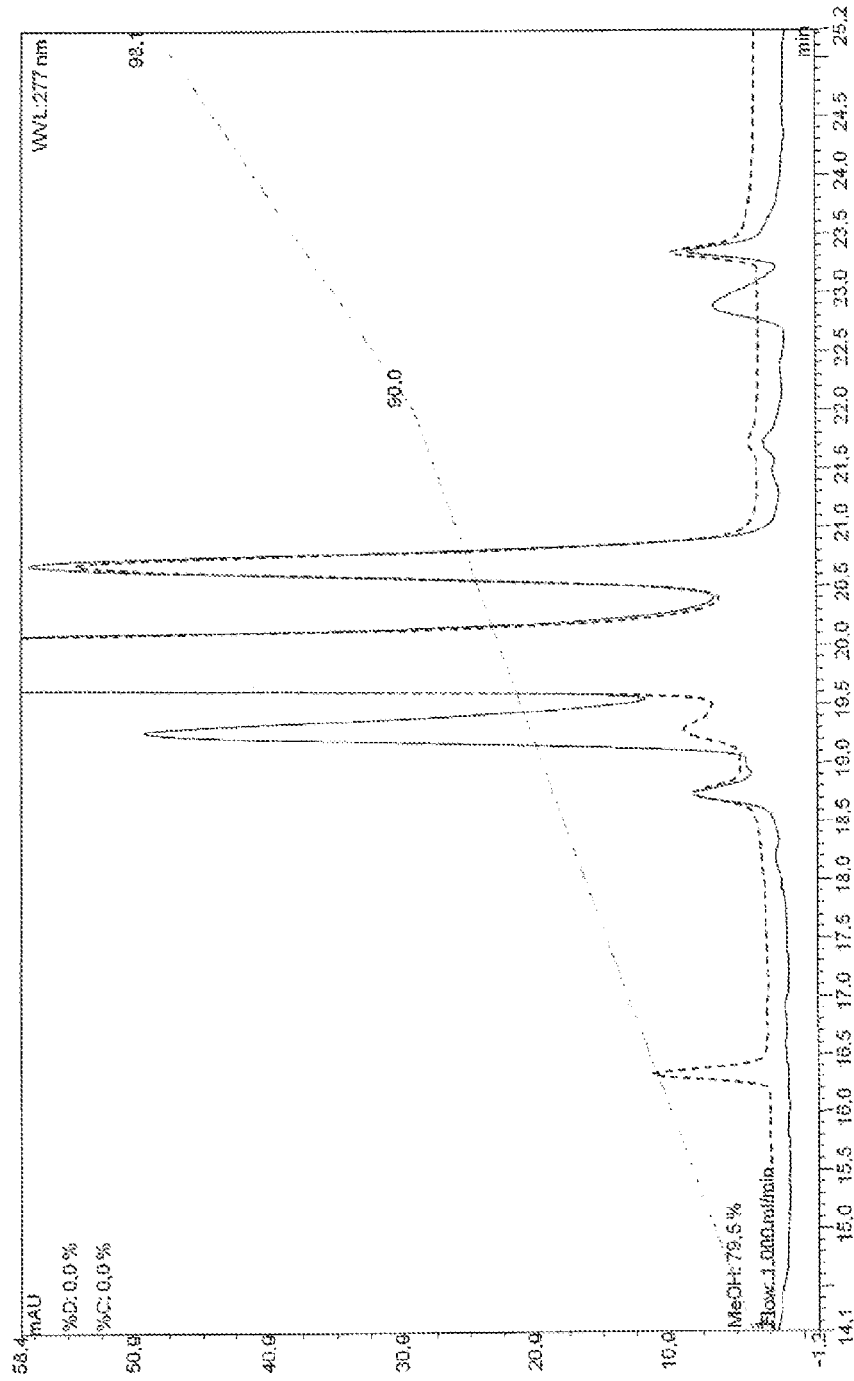

FIG. 2: Analytical chromatogram of the purified everolimus (broken line) compared to the crude mixture (continuous line).

Figure 3:
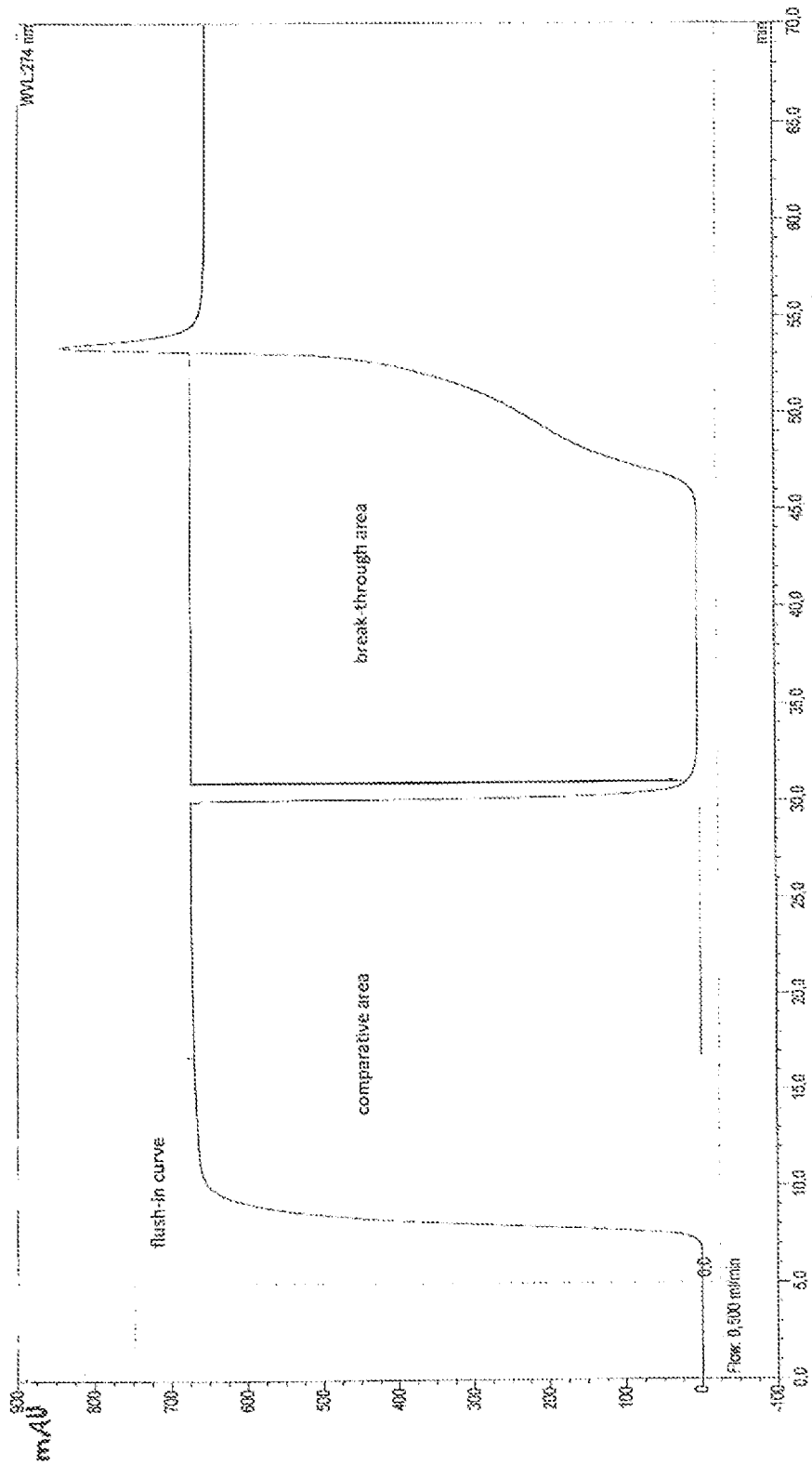

FIG. 3: Sample curve for the determination of the amount of amine groups by means of break-through measurement with 4-toluene sulfonic acid (front analysis).

Figure 4:
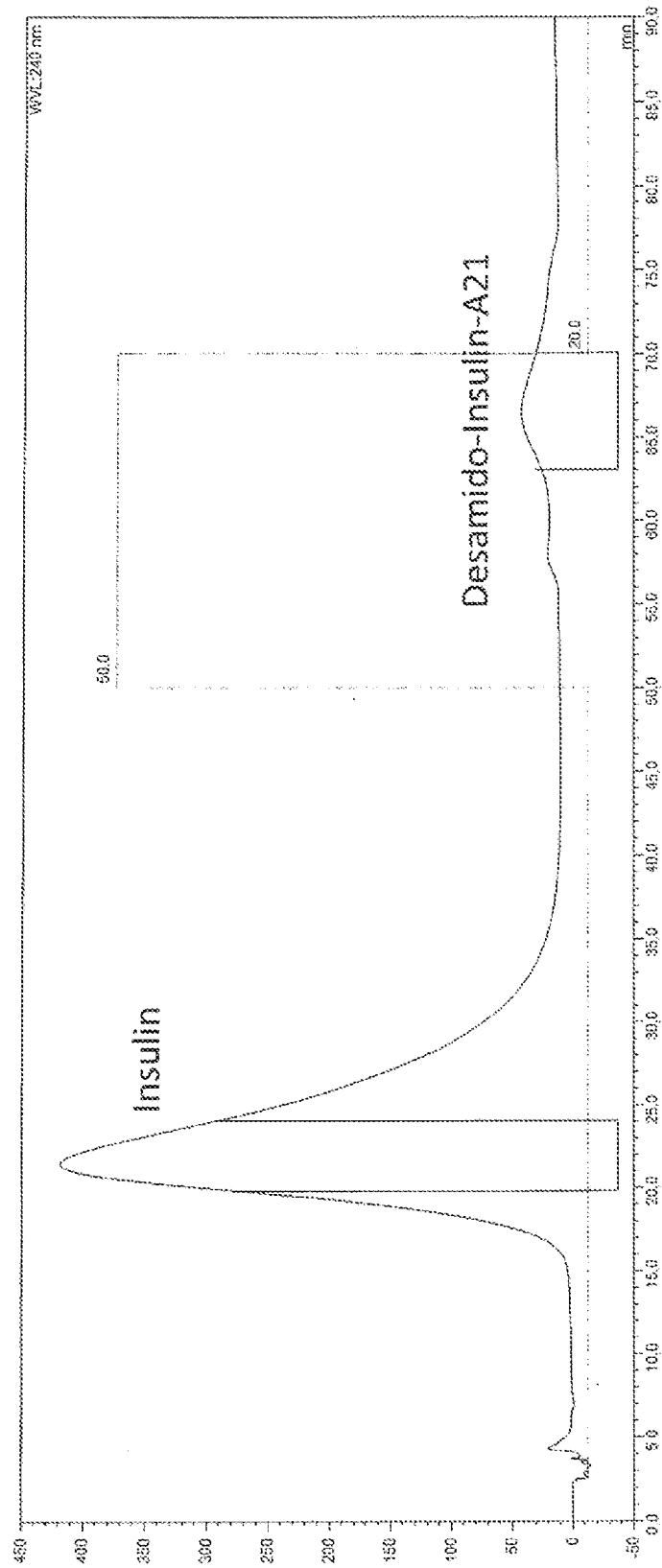

FIG. 4: Preparative chromatogram of the fractionation of Insulin and its byproduct Desamido-insulin-A21 according to the method in Example 1 by a sorbent according to the invention produced as in Example 3.

Figure 5:
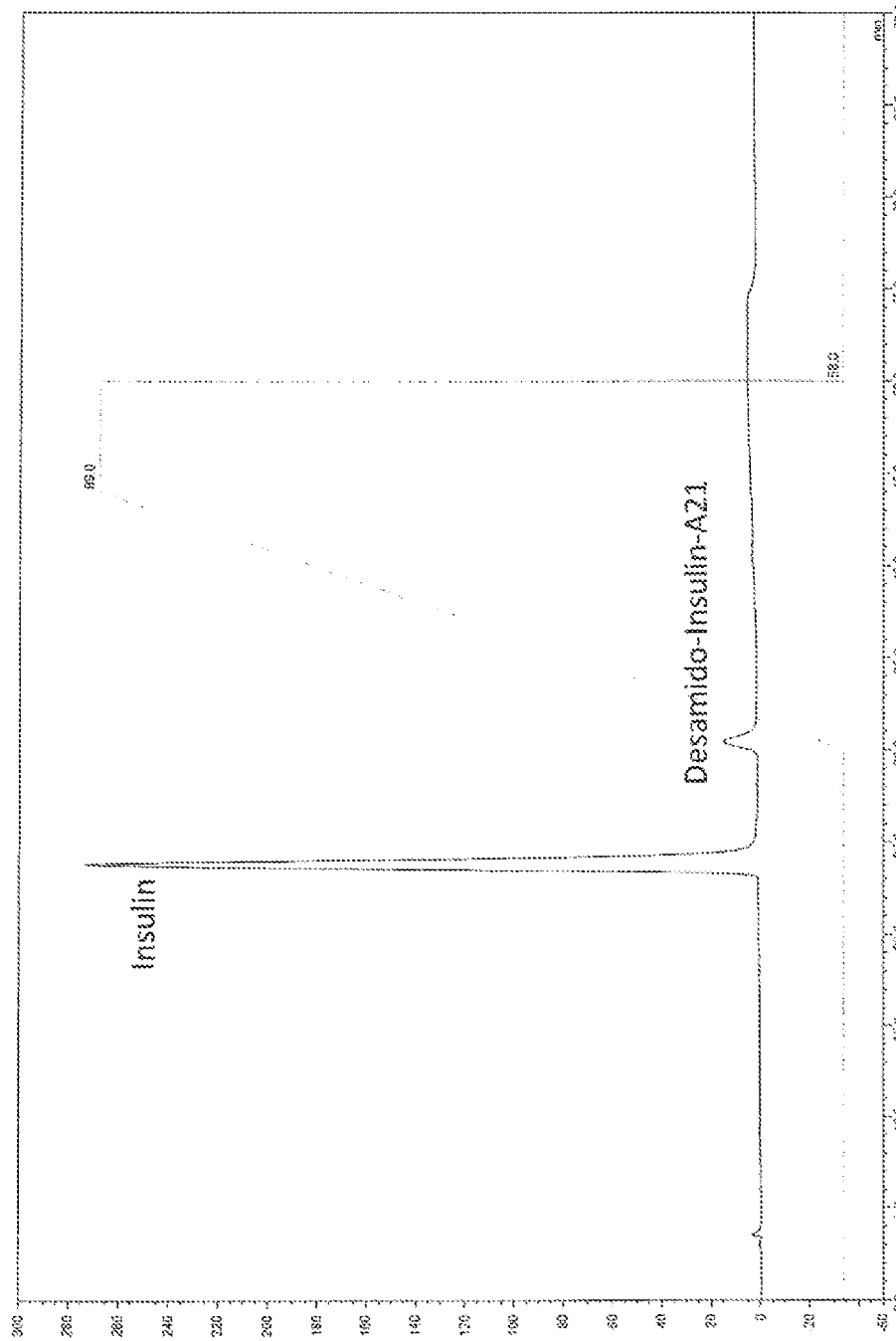

FIG. 5: Analytical chromatogram of the crude mixture of Insulin and Desamido-insulin-A21 applied as starting mixture in the separation method of Example 4.

Figure 6:
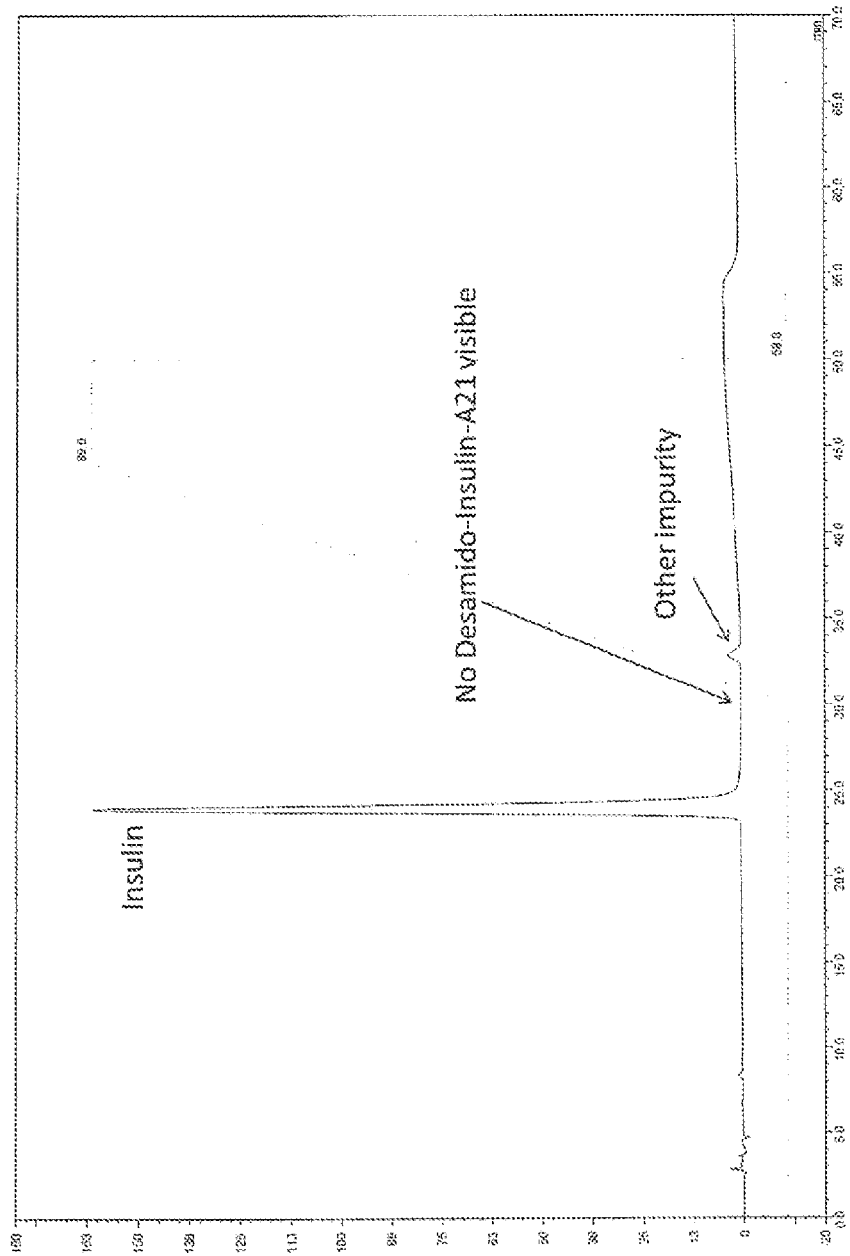

FIG. 6: Analytical chromatogram of the first fraction obtained by the separation method of Example 4.

Figure 7:
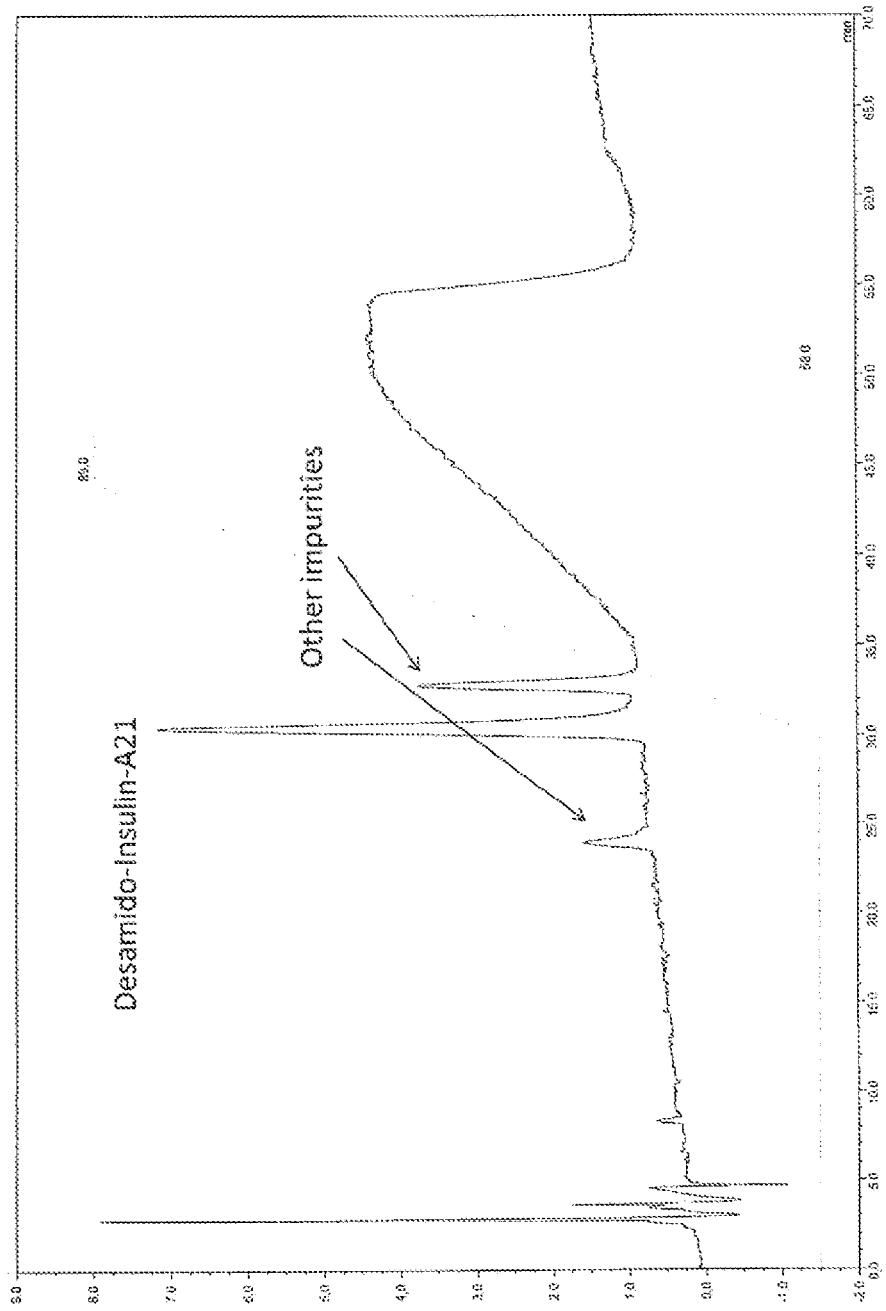

FIG. 7: Analytical chromatogram of the second fraction obtained by the separation method of Example 4.

EXAMPLES

Analytical Methods:
Determination of the amount of amine groups by means of break-through measurement with 4-toluene sulfonic acid (front analysis) (titration method):

The respective sorbent is packed to a column having the dimensions 33.5×4 mm (bed volume 0.42 mL). The filled column is then flushed with the following media at a flow rate of 1.0 mL/min:
5 mL of water
10 mL of a 100 mM aqueous solution of ammonium acetate
1 mL of water
10 mL of a 100 mM aqueous solution of trifluoroacetic acid
10 mL of water A base line is detected at a HPLC-device having a pump and a UV-detector after water has been pumped through the device for 5 min at 0.5 mL/min. After that a solution of 10 mM 4-toluene sulfonic acid in water is pumped through, whereas the extinction of the eluent is detected at 274 nm. The extinction rises in few minutes to a level of about 700 mAU and remains constant at this level (flush-in curve). After 25 min the column is applied between pump and detector and is flushed with 10 mM of 4-toluene sulfonic acid at 0.5 mL/min. The extinction then drops to 0 mAU since the column is binding 4-toluene sulfonic acid. If the capacity of the column is exhausted, the extinction of the eluate again rises to the starting level of ~700 mAU.

For the determination of the capacity of 4-toluene sulfonic acid the area below the level of the flush-in curve is integrated as comparative area, thereby obtaining the relationship between surface area and the amount of 4-toluene sulfonic acid. After that the area (break-through area) of the toluene sulfonic acid solution absorbed by the column is titrated, and the volume of the device and the dead volume of the column (0.5 mL) are subtracted. The break-through area directly indicates the amount of 4-toluene sulfonic acid bound to the column. Dividing this amount by the volume of the column yields in the capacity of toluene sulfonic acid per mL of the sorbent, also resulting in the amount of amine groups of the sorbent. For the better understanding of this method FIG. 3 shows such an example curve.

Example 1

Method of Producing a Sorbent According to the Invention Comprising Residues of the Following Formula

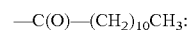
$-C(O)-(CH_2)_{10}CH_3$:

An aqueous solution of polyvinylamine (4.5 g in 300 g water, pH 8 adjusted by adding trifluoroacetic acid (TEA)) was given to 300 g of Daisogel SP120 10 P. The mixture was agitated on a sieve shaker for five hours and afterwards dried in vacuum at 50° C. After reaching constant weight the sorbent was suspended in 900 mL isopropanol and 3.64 g ethylene glycol diglycidyether in 50 mL was added. The mixture was stirred at 70° C. for 6 hours. Afterwards the sorbent was filtered off and washed with 600 mL isopropanol, 2400 mL 0.5 M TFA in water, 600 mL water, 600 mL dimethylformamide (DMF), 1800 mL 0.5 M triethylamine (TEA) in DMF and 600 mL DMF.

The amount of amine groups of the resulting intermediate determinable by titration was about 144 µmol/mL.

The sorbent was suspended again in 900 mL DMF and 12.0 g lauric acid, 22.8 g HBTU and 8.4 mL triethylamine were added. The mixture was stirred at 50° C. for 2 hours and filtered off afterwards. The sorbent was washed with 100 mL DMF, 300 mL 0.5 M TFA in DMF, 300 mL 0.3 M TFA in water, 100 mL water 100 mL DMF, 300 mL 0.5 M TEA in DMF, 100 mL water and 200 mL methanol. After drying in vacuum at 50° C. the sorbent is ready for use.

The resulting sorbent contains about 15 µmol/mL of free amine groups, determined via titration, and about 85 µmol/mL of the residues —C(O)—(CH$_2$)$_{10}$CH$_3$, determined via elemental analysis.

Example 2

Purification of Everolimus by Using the Sorbent Produced in Example 1

The sorbent produced in Example 1 was filled into a axially compressed ModCol-column of 25.4×250 mm bed size. A sample load of 1% was applied with a mobile phase of ethyl acetate/dichlorormethane 1/1 at 40 mL/min. The crude mixture essentially consisting of 80 to 85 weight-% everolimus and 15 to 20 weight-% rapamycin was fractionated according to FIG. 1. FIG. 2 shows the analytical chromatogram of the purified everolimus (broken line) compared to the crude mixture (continuous line). The results are also shown in the following Table 1:

TABLE 1

| | Everolimus | | Rapamycin | |
|---|---|---|---|---|
| Fraction | Purity [%] | yield [%] | Purity [%] | yield [%] |
| BT1 | 61.52 | 22 | 24.52 | 92 |
| BT2 | 99.08 | 5 | 0.81 | 0 |
| BT3 | 99.17 | 4 | 0.76 | 0 |
| BT4 | 99.34 | 47 | 0.6 | 3 |
| BT5 | 98.99 | 8 | 0.82 | 1 |
| BT6 | 98.77 | 6 | 1.04 | 1 |
| BT7 | 98.32 | 4 | 1.48 | 1 |
| BT8 | 94.23 | 4 | 5.27 | 3 |

Rapamycin is the main impurity. When combining the fractions BT2 to BT7 everolimus could be obtained in 99.18% purity and 73% yield.

Sorbents similarly produced according to Example 1 comprising less than 5 µmol/mL of free amine groups lead to purities of much less than 99% and a yield of much less than 70% of the obtainable everolimus. In the same way sorbents comprising more than 190 µmol/mL of free amine groups also lead to purities of much less than 99% and a yield of much less than 70% of the obtainable everolimus.

In the same way, sorbents having a molar ratio of the residues according to formula (I) to the amount of functional groups of the polymer (before derivatization) of less than 0.4 or more than 0.8 are more than 20% deteriorated with respect to the purity and yield of the obtainable everolimus. Sorbents, wherein the same range is less than 0.5 or more than 0.7 are more than 30% deteriorated with respect to the purity and yield of the obtainable everolimus, since the retention is too low.

Example 3

Method of Producing a Sorbent According to the Invention Comprising Residues of the Following Formula

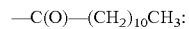
—C(O)—(CH$_2$)$_{10}$CH$_3$:

An aqueous solution of polyvinylamine (30 g in 400 g water, pH $ adjusted by, adding hydrochloric acid (HCl)) was given to 600 g of Daisogel SP120-10 P. The mixture was agitated on a sieve shaker for six hours and afterwards dried in vacuum at 50° C. After reaching constant weight the sorbent was suspended in 3000 mL isopropanol and 12.1 g ethylene glycol glycidylether in 150 mL isopropanol was added. The mixture was stirred at 55° C. for 6 hours. Afterwards the sorbent was filtered off and washed with 3000 mL isopropanol, 9000 mL 0.1 M in water, 3 000 mL water and 4500 mL methanol. The sorbent was stored dry until further use.

The amount of amine groups of the resulting intermediate determinable by titration was about 316 µmol/mL.

50 g of the sorbent was washed with 300 ml dimethylene formamide (DMF), 300 mL 0.5 M triethylene amine (TEA) in DMF and 300 mL DMF again. Finally, it was suspended in 150 mL DMF and 5.0 g lauric acid, 9.5 g HBTU and 3.4 mL triethylamine were added. The mixture was stirred at 50° C. for 4 hours and filtered off afterwards. The sorbent was washed with 300 mL DMF, 300 mL 0.1 M HCl in DMF, 300 mL 0.1 M HCl in water, 300 mL water and 300 mL methanol. After drying in vacuum at 50° C. the sorbent is ready for use.

The resulting sorbent contains about 173 µmol/mL of free amine groups, determined via titration, and about 202 µmol/mL of the residues —C(O)— (CH$_2$)$_{10}$CH$_3$, determined via elemental analysis.

Example 4

Purification of Insulin by Using the Sorbent Produced in Example 3

A crude sample comprising insulin and as main impurity desamido-insulin-A21 (3 mg/mL water/acetonitrile/trifluoroacetic acid (95/5I0.1) is separated using a Bionex HPLC system consisting of a four channel low-pressure gradient pump (LPG 580, LPG 680 or LPG 3400), auto sampler (Gina 50, ASI-100 or WP-300), six-channel column switching valves (Bests), column oven and a diode-array uv detector (UVD 170U, UVD 3408 or NAND 3400). The sorbent was filled in a 250×4 mm steel column. For purification different gradients of three eluents were used as can be seen from Table 2 below. The first eluent is 10 mM NaKHPO$_4$ in water, the second eluent a solution of 10 mM NaKHPO$_4$/1 M NCl in water and the third eluent is 1 propanol. The flow rate was 1 mL/min. The injection volume was 1 mL.

FIG. 4 shows the course of fractionation.

TABLE 2 gradient of three different eluents

| Time [min] | 10 mM NaKHPO4 (7.3) | 10 mM NaKHPO4, 1M NaCl (7.3) | 1-Propanol |
|---|---|---|---|
| 0 | 70 | 10 | 20 |
| 0 | 70 | 10 | 20 |
| 50 | 70 | 10 | 20 |
| 50 | 30 | 50 | 20 |
| 70 | 30 | 50 | 20 |
| 70 | 70 | 10 | 20 |
| 90 | 70 | 10 | 20 |

FIG. 4 shows that a very good separation can be obtained when using the sorbent according to Example 3. Insulin is eluted from the column more than 40 minutes earlier than Desamido-insulin-A21. That is, the retention of Desamido-insulin-A21 on the sorbent according to the invention is very high compared to the retention of insulin.

Analytical chromatogram of the crude mixture of Insulin and Desamido-insulin-A21 applied as starting mixture in the separation method of Example 4.

Analysis of the separation according to the method of Pharmakopoe as known in the art using a YMC Pack, Pro C18, 250×4.5 mm, 12 nm (Mobile Phases: Buffer A: 100 ml acetonitrile, 700 ml water, 200 ml sulphate buffer solution pH 2.0 R, Buffer B: 400 ml acetonitrile, 400 ml water, 200 ml sulphate buffer solution pH 2.0 R) shows for the crude mixture in the analytical chromatogram that Desamido-insulin-A21 is eluted after 30 min.

The first fraction by using the method according to the invention shows in the analytical chromatogram no elution of Desamido-insulin-A21 after 30 min (FIG. 6). The analytical chromatogram of the second fraction of the method according to the invention, however, shows the elution Desamido-insulin-A21 (FIG. 7). The analytics shows the quality of the separation of Insulin from Desamido-insulin-A21.

Sorbents similar produced as in Example 3 having a molar ratio of the residues according to formula (I) to the amount of functional groups of the polymer (before derivatization) (derivatization degree) of less than 0.4 does not lead to a baseline separation of Insulin and Desamido-insulin-A21 due to the worse retention of the Desamido-insulin-A21 In the same way sorbents having a derivatization degree of more than 0.8 also allow no baseline separation of the two substances due to the good retention of insulin, Sorbents wherein the same ratio is less than 0.5 or more than 0.7 allow separation of the two substance, but in yields of less than 50% with regard to the insulin.

In the same way sorbents having from 5 µmol/mL to 190 µmol/mL of free amine groups lead to baseline separation of Insulin and Desamido-insulin-A21, wherein sorbents having free amine groups of less than 5 µmol/mL or more than 190 µmol/mL show no baseline separation of Insulin and Desamido-insulin-A21, i.e. pure yields.

The invention claimed is:

1. A sorbent for the purification of organic molecules exhibiting both a hydrophilic and a hydrophobic moiety, the sorbent comprising a solid support material, wherein the surface of the solid support material comprises a residue of the following general formula (I):

formula (I), wherein the residue is attached via a covalent single bond represented by the dotted line in formula (I) to a functional group on the surface of a polymer film on the surface of the solid support material, wherein the polymer of the polymer film comprises individual chains which are covalently crosslinked with each other, and wherein the individual chains are not covalently bound to the surface of the solid support material, wherein the polymer is a polyvinylamine, and wherein:

(a) L represents a covalent single bond or is a bivalent unit selected from the group consisting of —C(O)—, —S(O)$_2$—, and —CH$_2$CH(OH)—;

(b) X represents a linear C$_6$-C$_{15}$ alkyl.

2. The sorbent of claim 1, wherein L is —C(O)—.

3. A method for the purification of organic molecules, comprising contacting organic molecules with the sorbent of claim 1.

4. The method of claim 3, wherein the organic molecules are pharmaceutically active compounds.

5. The method of claim 3, wherein the organic molecules exhibit both a hydrophilic and a hydrophobic moiety.

6. The method of claim 3, wherein the organic molecules are selected from the group consisting of everolimus, insulin, and endotoxins.

* * * * *